United States Patent
Novitski et al.

(10) Patent No.: US 11,292,722 B2
(45) Date of Patent: Apr. 5, 2022

(54) TREATMENT OF SPENT CANNABIS BIOMASS

(71) Applicant: Nextleaf Solutions Ltd., Coquitlam (CA)

(72) Inventors: David Michael Novitski, Burnaby (CA); Xuan Jia, Burnaby (CA)

(73) Assignee: Nextleaf Solutions Ltd., Coquitlam (CA)

( * ) Notice: Subject to any disclaimer, the term of this patent is extended or adjusted under 35 U.S.C. 154(b) by 244 days.

(21) Appl. No.: 16/705,842

(22) Filed: Dec. 6, 2019

(65) Prior Publication Data
US 2021/0171355 A1    Jun. 10, 2021

(51) Int. Cl.
*C01B 32/324* (2017.01)
*B01J 20/20* (2006.01)
*C01B 32/336* (2017.01)
*C07D 311/78* (2006.01)

(52) U.S. Cl.
CPC .............. *C01B 32/324* (2017.08); *B01J 20/20* (2013.01); *C01B 32/336* (2017.08); *C07D 311/78* (2013.01)

(58) Field of Classification Search
CPC ... C01B 32/324; C01B 32/336; C07D 311/78; B01J 20/20
See application file for complete search history.

(56) References Cited

U.S. PATENT DOCUMENTS

2004/0147767 A1*  7/2004  Whittle ............. B01D 11/0273
                                                      549/390
2018/0296616 A1* 10/2018  Rivas .................. A61K 36/185

FOREIGN PATENT DOCUMENTS

CN          110294476 A    * 10/2019

OTHER PUBLICATIONS

Lupul, Iwona, et al. "Tailoring of porous texture of hemp stem-based activated carbon produced by phosphoric acid activation in steam atmosphere." Journal of Porous Materials 22.1 (2015): 283-289.*
English machine translation of CN110294476A (Year: 2019).*
Reed, Anton R., and Paul T. Williams. "Thermal processing of biomass natural fibre wastes by pyrolysis." International Journal of Energy Research 28.2 (2004): 131-145.*
Rodríguez-Reinoso, F., et al. 1992. Activated carbons from lignocellulosic materials by chemical and/or physical activation: an overview. in: Carbon, vol. 30, No. 7.
Oginni, O. 2018. Characteristics of activated carbons produced from herbaceous biomass feedstock. in: Wood Science and Technology, vol. Ph.D., West Virginia University. Morgantown, WV.

* cited by examiner

*Primary Examiner* — Richard M Rump
(74) *Attorney, Agent, or Firm* — Damien G. Loveland

(57) ABSTRACT

Spent cannabis biomass is heated in stages, the first to remove water and volatile components, and the second to reclaim leftover cannabinoids. During a third, higher temperature stage, the biomass is subjected to a $CO_2$ and/or water vapor treatment in order to obtain activated carbon with a desired porosity level.

18 Claims, 2 Drawing Sheets

TREATMENT OF SPENT CANNABIS BIOMASS

TECHNICAL FIELD

Spent cannabis biomass is treated in order to be recycled and reduce waste. More specifically, spent cannabis biomass is heated to reclaim residual cannabinoids and leave activated carbon.

BACKGROUND

The growth of cannabis production in the world poses a considerable problem, i.e. how to properly dispose of the waste biomass. Currently, licensed cannabis producers send waste biomass to landfills, however, as production increases, the volume of waste biomass has the potential to become too large for current waste management infrastructure to deal with. In addition, as more companies start to grow and/or process cannabis, the increased supply will inevitably reduce the price for this commodity as has been seen in USA state jurisdictions such as Oregon. As the cannabis industry matures in the world, it will be important for companies to adopt ways to maintain revenue. The reuse/recycling of waste biomass could be used to offset the reduction in cannabis commodity prices.

The process of cannabinoid extraction, regardless of method, whether it be carbon dioxide ($CO_2$) or ethanol extraction, for example, is complicated in a commercial setting. This is due to the problem of obtaining sufficient return on investment in processing. During processing, cannabinoids can be left in spent cannabis biomass due to either cannabinoid saturation in a single solvent extraction pass or because it is more cost effective in terms of output of oil per day to stop the process with a "mostly spent" batch, and start with fresh biomass.

In possibly the most extreme case, when using $CO_2$ extraction, 20% of cannabinoids may be left in the waste biomass. These cannabinoids are typically unrecovered as it saves time during production to start with a fresh batch of cannabis which allows for 80% extraction. In ethanol extraction, around 5% of cannabinoids, or more, may remain in the waste biomass. As a result, the spent cannabis biomass needs to be denatured and disposed of, which leads to lost product throughout the industry.

This background is not intended, nor should be construed, to constitute prior art against the present invention.

SUMMARY OF INVENTION

Waste cannabis biomass from a cannabis extraction process is recycled into activated carbon, which is widely used as a purification/adsorption material in industry, including the cannabis industry. This invention therefore creates an opportunity to denature spent cannabis biomass into a valuable commodity, activated carbon, and avoid a waste stream going directly into landfills or the environment. The production of activated carbon also fulfills the regulatory requirements of destroying spent cannabis biomass.

The invention can also potentially cut the cost of the waste management of cannabis companies. Also, the treatment described herein is generally a low-cost process compared to other methods of producing activated carbon.

For the recycling treatment, spent cannabis biomass is put into an oxygen-free fixed bed reactor and subjected to a series of high temperatures (from about 100 to 1000° C.) for a period of time (about 4 to about 8 hours), with a gas treatment. The gas treatment may use $CO_2$ or water vapor.

The present invention also aims to recover the leftover cannabinoids as an oil during the process of converting the spent cannabis biomass to activated carbon. Considering that production-scale operations deal with hundreds of kilograms of biomass per day, capturing the remaining cannabinoids, which would otherwise be disposed of, would result in an appreciable recovery over time.

Disclosed herein is a process for treating spent cannabis biomass comprising, in an oxygen-free atmosphere: raising the spent cannabis biomass to a first temperature that is sufficient to remove water and volatile components from the spent cannabis biomass; raising the spent cannabis biomass to a second temperature that is sufficient to reclaim cannabinoids from the spent cannabis biomass, wherein the second temperature is higher than the first temperature; raising to a third temperature the spent cannabis biomass, wherein the third temperature is higher than the second temperature; and injecting $CO_2$ and/or water vapor into the spent cannabis biomass while the spent cannabis biomass is above the second temperature; thereby transforming the spent cannabis biomass into activated carbon.

BRIEF DESCRIPTION OF THE DRAWINGS

The following drawings illustrate embodiments of the invention, which should not be construed as restricting the scope of the invention in any way.

DESCRIPTION

A. Glossary

The term "activation" may refer to a process for biomass to be transformed into activated carbon. In the present invention, the activation is a physical process that involves heating and gas treatment to transform the biomass into activated carbon, also known as activated charcoal.

The term "cannabinoids" may refer to a group of chemicals that act on cannabinoid receptors in the body, numerous of which are found in the cannabis plant.

The term "spent" in relation to cannabis biomass may refer to cannabis biomass that has been subjected to at least one extraction process and has thereby had at least some of its cannabinoids removed.

B. Overview

Figures 1, 2:
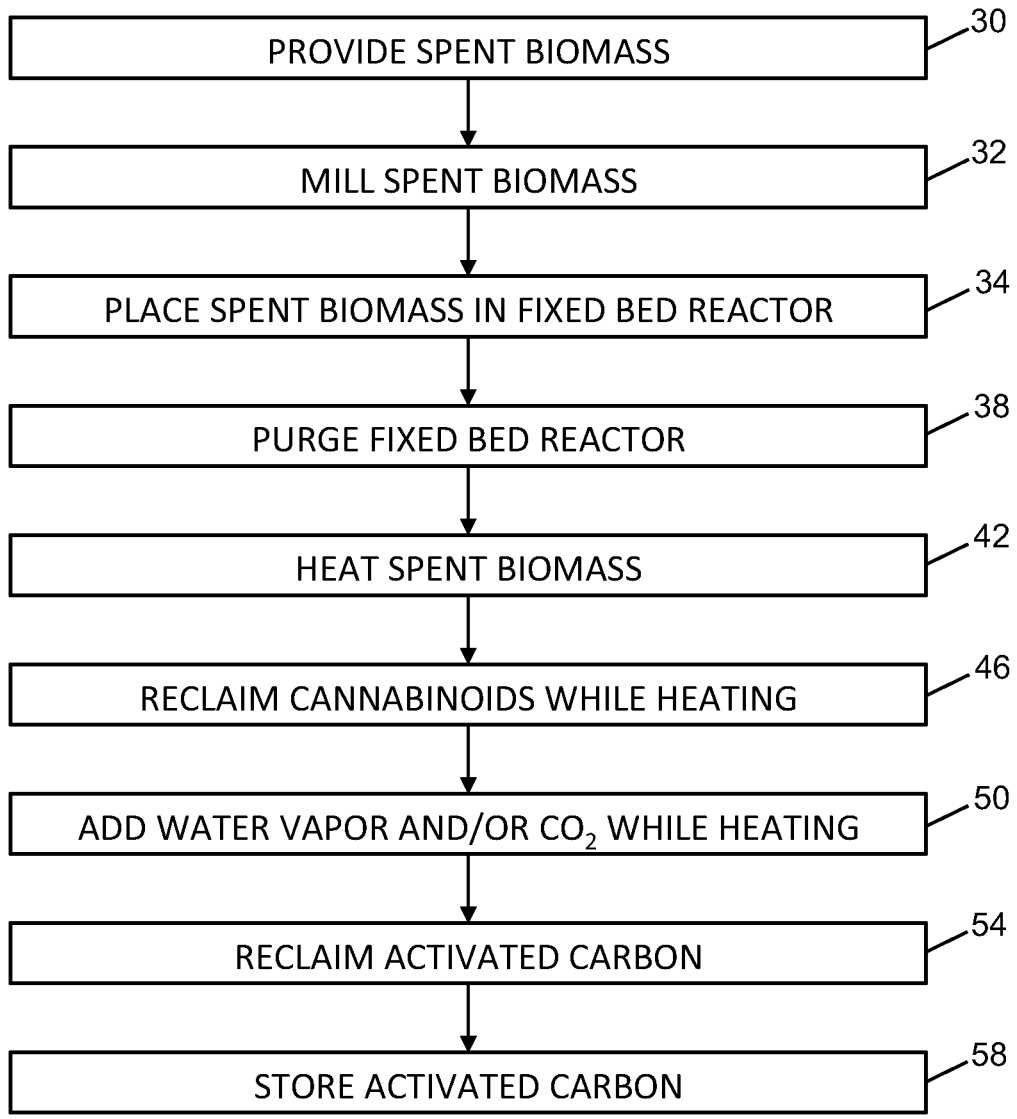
FIG. 1 is a high-level flowchart describing the process for the treatment of spent cannabis biomass according to an embodiment of the present invention.
FIG. 2 is a detailed flowchart describing the process used for the treatment of spent cannabis biomass according to an embodiment of the present invention.

FIG. 1 shows a high-level flowchart describing the process used for the treatment of spent cannabis biomass. In step 2, the spent cannabis biomass is provided from a cannabis extraction process. After that, in step 4, cannabinoids are reclaimed from the spent cannabis biomass by heating. Then, in step 6, the spent cannabis biomass is activated physically by heating it to a higher temperature and injecting water vapor and/or $CO_2$ into it.

C. Exemplary Embodiment

Referring to FIG. 2, the spent cannabis biomass is provided in step 30. Then, in step 32, the spent cannabis biomass is optionally milled using a milling machine. In some embodiments, the spent cannabis biomass is milled to an average particle size of below 2 mm, for example to provide accessibility to increased surface area. Milling is not typically necessary, as the cannabis has often been previously ground for the prior extraction process. The particle size of the spent cannabis biomass has an influence on the treatment. For example, the consistency of the milled spent cannabis biomass may cause pressure changes in the fixed bed reactor, which may lead to a higher energy consumption during the process.

In step 34, the milled spent cannabis biomass is placed in a fixed bed reactor.

The atmosphere in the fixed bed reactor is purged to remove oxygen in step 38. For example, the purge of the fixed bed reactor atmosphere is achieved by injecting nitrogen gas or other inert gas. The inert gas is injected into the fixed bed reactor in such a way that a continuous flow is created inside the fixed bed reactor during both the purge and the subsequent heating stages.

The temperature of the fixed bed reactor is set to reach a final temperature between 800° C. and 1000° C. in step 42. In some embodiments, various different heating rates and heating profiles are implemented to reach the final temperature. A controlled heating profile is applied such that known components are made to leave the milled spent cannabis biomass at a desired time. The milled spent cannabis biomass is treated in the fixed bed reactor for an overall duration of 4 to 8 hours, for example. As the temperature of the fixed bed reactor increases, and approaches about 100° C., water or solvent present in the cannabis biomass evaporate from the biomass.

During step 46, with continued heating, cannabinoids are collected from the heated, milled spent cannabis biomass prior to reaching the uppermost set temperature. Above about 170° C., cannabinoids start to evaporate. When the milled spent cannabis biomass is exposed to a temperature above 230° C., most of the cannabinoid components from the milled spent cannabis biomass are vaporized.

In step 46, the temperature in the fixed bed reactor is maintained constant, for example at 500° C., to vaporize all the cannabinoids from the milled spent cannabis biomass. The vaporized cannabinoids are collected using a cold trap or condenser. The cold trap may contain cold ethanol in order to capture the vaporized cannabinoids, to form a mixture of crude oil and ethanol. In some embodiments, the target temperature for step 46 is chosen in order to selectively capture one or more different cannabinoids. In that embodiment, the target temperature corresponds to the boiling point of the targeted cannabinoid. The targeted cannabinoid is then vaporized and passed through the cold trap to be captured from the inert gas flow.

In some embodiments, the mixture of crude oil and ethanol may be subsequently centrifuged or run through a rotary evaporator or falling film evaporator to remove the ethanol. In some embodiments, various filtration processes such as membrane filtration and/or activated charcoal filtration are implemented to refine the crude oil. In some embodiments, the crude oil may be distilled with a distillation setup such as a film wipe distillation or spinning band fractional distillation to refine the crude oil, remove impurities and/or separate cannabinoids from each other.

During step 50, $CO_2$ and/or water vapor are introduced into the fixed bed reactor when the temperature in the reactor is equal to or above 500° C., after the cannabinoids are evaporated and reclaimed. In some embodiments, in step 50, $CO_2$ and/or water vapor are introduced into the fixed bed reactor after the milled spent cannabis biomass has been exposed to the high temperature (500° C.) for a substantial time (e.g. over half an hour), in step 46. In some embodiments, the milled spent cannabis biomass is also pressurized during the heating phase. $CO_2$ and/or water vapor are injected into the fixed bed reactor as a continuous flow. $CO_2$ and/or water vapor are injected into the fixed bed reactor at a flow rate between 100-3000 mL/min, depending on the volume of the fixed bed reactor. The overall flow rate of the introduced $CO_2$ and/or water vapor therefore varies in regard to the fixed bed reactor setup rather than the amount of milled spent cannabis biomass to be treated.

During the treatment, the milled spent cannabis biomass loses its non-carbon elements. These elements, when subjected to high temperatures, are expelled from the milled spent cannabis biomass in the form of gases or tar. As a result, the remaining material in the fixed bed reactor is carbon with a structure that is known as activated carbon. An assembly of aromatic sheets and strips provides the overall structure of the activated carbon. The porosity of the activated carbon is defined by the spaces or pores located between the main structural elements of the activated carbon. In some embodiments, the tar is also collected during the treatment.

In step 50, the injection of $CO_2$ and/or water vapor facilitates the increase of the size of the pores in the resulting activated carbon. In contrast, the treatment of the milled spent cannabis biomass without the $CO_2$ and/or water vapor treatment would tend to result in biochar, which is a non-porous, low surface area product.

In some embodiments, $CO_2$ is considered better than water vapor as it is simpler to handle, clean, and has a slower reaction rate at the operating/reacting temperatures (~500 to 800° C.). Water vapor activation results in a lower homogeneity due to a less controlled gasification, which results in a lower yield.

In some embodiments, $CO_2$ is mixed with water vapor. The variation of the mixing ratio between $CO_2$ and water vapor results in different levels of porosity in the obtained activated carbon. The mixing ratio can vary from almost 100% $CO_2$ to almost 100% water vapor. In some embodiments, the $CO_2$ is used separately from the water vapor, either before or after.

In step 54, after cooling, the activated carbon is collected from the fixed bed reactor. The activated carbon is then stored at room temperature in step 58. Optionally, the activated carbon is stored in an environment with a low humidity index.

In some embodiments, the collected activated carbon has a surface area between 600 and 3000 $m^2/g$. In some embodiments, additional treatments are applied to increase the purity of the activated carbon.

The purity of the collected activated carbon is usually at least 90%. The conditions responsible for the purity of the activated carbon are the initial consistency of the milled spent cannabis biomass, the temperature of the treatment, the gas used for the treatment, the heating profile and the duration of the treatment. With the use of $CO_2$, most of the impurities initially contained in the milled spent cannabis biomass are expelled during the treatment.

The yield of the treatment is between 10 and 50% of the initial dry spent cannabis biomass weight. This yield depends on the consistency of the initial milled spent cannabis biomass and the treatment conditions such as the temperature and the duration.

Figure 3:
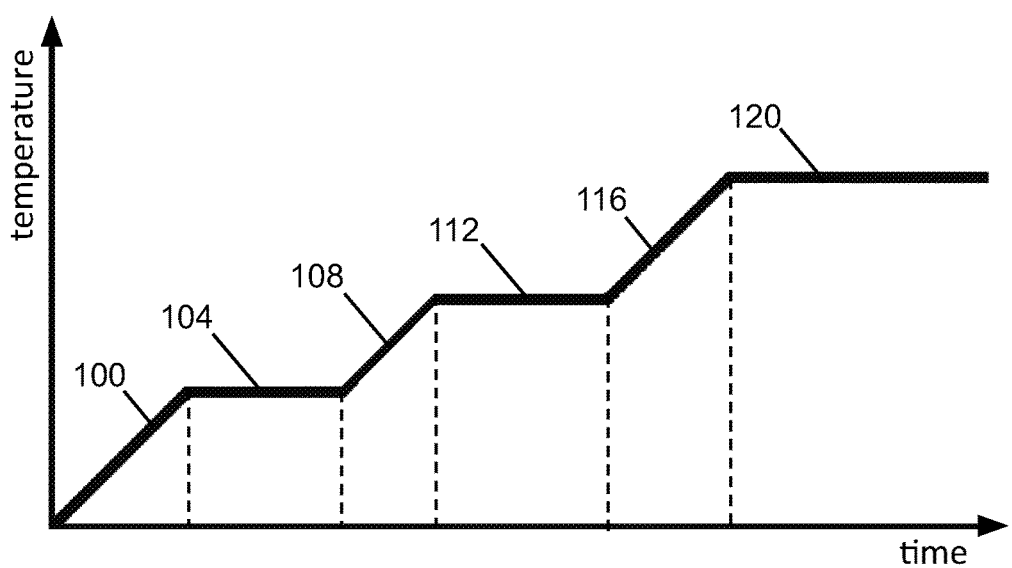
FIG. 3 is a graph representing the heating profile for the treatment of spent cannabis biomass according to an embodiment of the present invention.

Referring to FIG. 3, there is shown a graph representing an exemplary heating profile of the treatment. In step 100, the milled spent cannabis biomass is heated to a temperature of about 100° C. to release water and low boiling point 100° C.) volatile components from the milled spent cannabis biomass. Water and these volatile components are directed to bypass the cold trap, so that they are removed from the fixed bed reactor without being captured. In some embodiments, the volatile components and water are captured via an additional cold trap for waste disposal purposes or other usage. Step 100 is the first step of the gasification process. In step 104, the temperature is maintained at 100° C. for over half an hour, for example, in order to evaporate all the water and low boiling point volatiles.

In other embodiments, other temperatures may be used for step 104, provided that they allow the water and low boiling point volatiles to evaporate from the spent cannabis biomass without evaporation of the cannabinoids that are to be reclaimed in a later step.

In step 108, the cold trap is engaged, and the milled spent cannabis biomass is further heated to a temperature of 500° C. in order to evaporate the cannabinoids contained in the milled spent cannabis biomass. Most of the cannabinoids have a boiling point that is in the region of 120-175° C.; however, when vaporizing cannabinoids, temperatures in the range 170-230° C. are typically used. While these lower temperatures may be used in some embodiments, it is useful in other embodiments to use higher temperatures, in the range 230-500° C., in order to reduce the time and increase the efficiency of the process.

In step 112, the temperature of 500° C. is maintained for a substantial time (e.g. over half an hour) in order to reclaim all of the cannabinoids from the milled spent cannabis biomass. This is the second part of the gasification process. The duration of step 112 is related to the quality of the initial milled spent cannabis biomass. The vaporized cannabinoids are captured by condensation in the cold trap, with cold ethanol. The inert gas (e.g. nitrogen) passes through the oven to carry the vaporized cannabinoids that leave the heated spent cannabis biomass, and to bubble through the cold ethanol. As a result, the vaporized cannabinoids dissolve in the ethanol to form a mixture of crude oil and ethanol.

In other embodiments, other temperatures may be used for step 112, provided that they allow the cannabinoids that are to be reclaimed to evaporate from the spent cannabis biomass without significant degradation.

In some embodiments, a high surface area condenser is used to capture the cannabinoids instead of a cold trap. After the cannabinoids have been captured on the cold condenser, the condenser is subsequently removed and heated in order to collect the cannabinoids.

After the cannabinoids have been recovered, the milled spent cannabis biomass is heated from a temperature of 500° C. to a temperature of 800° C. in step 116. During step 116, $CO_2$ and/or water vapor are injected in order to activate the carbon. The injection of $CO_2$ and/or water vapor gradually increases the spaces between the structural elements in the biomass during its transition to activated carbon. In some embodiments, the start and end temperatures for step 116 are different.

In step 120, the temperature in the fixed bed reactor is maintained at 800° C. for 1 hour in order to convert the milled spent cannabis biomass to activated carbon. In some embodiments, the duration of step 120 is optimized to obtain a desired porosity of the final activated carbon. In some embodiments, the temperature of step 120 is different, as long as it is sufficiently high to complete the formation of the activated carbon from the spent cannabis biomass. In some embodiments, $CO_2$ and/or water vapor continue to be injected during step 120.

In some embodiments, the specific time and heating rate for each heating ramp and the target temperature for each step may require optimization to convert the totality of the milled spent cannabis biomass to activated carbon. In addition, the target temperature for each step may also require optimization to increase the overall efficiency of the process.

In some embodiments, if carrying out the treatment with $CO_2$ gas, a secondary or tertiary cold trap with a sufficiently low temperature could be used to capture $CO_2$ emissions from the process (at about −80° C., solid $CO_2$ directly deposits from the gaseous phase).

The cannabinoid crude oil is recovered from steps 108, 112 and further refined using distillation procedures such as film wipe distillation, if necessary. Different extraction/purification procedures are used for different makeups of incoming crude oil. Crude oil from ethanol extraction would have some trace ethanol volatiles, whereas crude oil from $CO_2$ extraction would not, so the distillation profile would change accordingly.

D. Exemplary Apparatus

Figure 4:
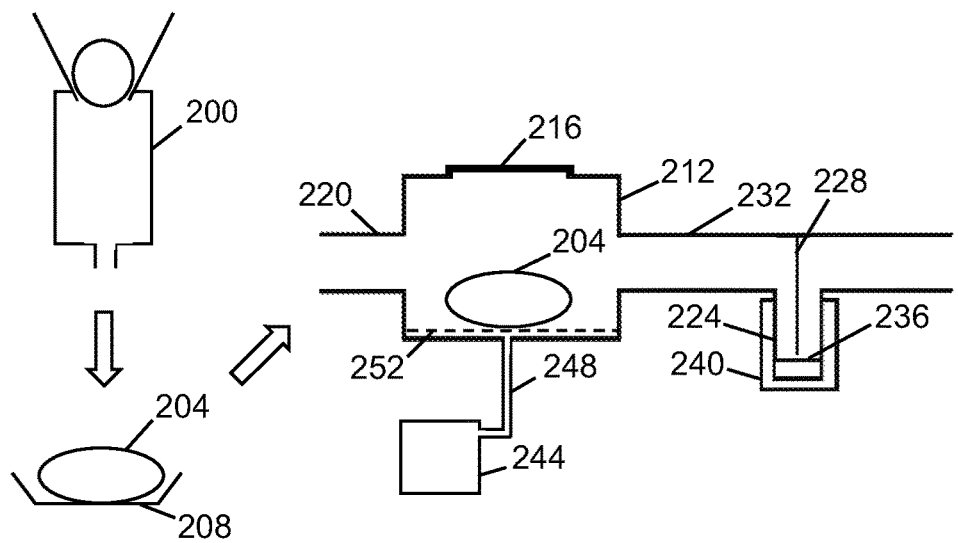
FIG. 4 is a schematic diagram of the apparatus used for the treatment of spent cannabis biomass according to an embodiment of the present invention.

Referring to FIG. 4, the spent cannabis biomass is optionally loaded into a milling machine 200. In some embodiments, other techniques or ways of reducing the size of the spent cannabis biomass may be used. For example, an impact crusher, pulverizers, breakers, or grinders may be used. The milled spent cannabis biomass 204 is collected on a tray 208.

The milled spent cannabis biomass 204 is placed into the fixed bed reactor 212 via an opening at the top, which is closed with a lid 216. In some embodiments, a heat furnace, a tube reactor, a kiln, a moving bed reactor, a trickle-bed reactor, a rotating bed reactor or a fluidized bed reactor is used in place of the fixed bed reactor 212 for the treatment.

The fixed bed reactor 212 is then purged to remove oxygen by injecting an inert gas such as nitrogen via an inlet 220 located on the reactor. The inert gas is injected continuously into the fixed bed reactor 212 during the subsequent steps.

The temperature in the fixed bed reactor 212 is raised to 100° C. During this first heating ramp, the cold trap or condenser 224 is disengaged from the fixed bed reactor 212 so that the water vapor and low boiling point volatile components evaporating from the milled spent cannabis biomass 204 are not captured. A bypass system 228 (e.g. a baffle, door or flap) is used in order to engage or disengage the cold trap 224 in the exhaust line 232 of the fixed bed reactor 212. In some embodiments, one or more additional cold traps (not shown) are mounted in the exhaust line 232 downstream of the cold trap 224. The temperature of the fixed bed reactor 212 is maintained at 100° C. for sufficient time to evaporate all the water and low boiling-point volatile components from the milled spent cannabis biomass 204.

After that, the temperature is raised to 500° C. During this second heating ramp, the cold trap 224 is engaged in the exhaust line 232 in order to capture the evaporated cannabinoids from the milled spent cannabis biomass 204. The inert gas flow through the fixed bed reactor directs the evaporated cannabinoids towards the cold trap 224. The evaporated cannabinoids with inert gas bubble through cold ethanol 236 contained in the cold trap 224. The evaporated cannabinoids dissolve in the cold ethanol 236 to form a mixture of crude oil and ethanol. The cold ethanol 236 in the cold trap 224 is maintained at a cold temperature (i.e. from 0° C. to −40° C.) using a cooling system 240 on the cold trap, such as a cooling jacket containing solid $CO_2$ or liquid nitrogen. The temperature in the fixed bed reactor 212 is then maintained at 500° C. to vaporize all the cannabinoids from the milled spent cannabis biomass 204, while retaining the cold trap 224 in the path of the exhaust line 232. After that, the mixture of ethanol and crude oil is removed from the cold trap 224 and collected. In some embodiments, the collected mixture is refined in order to collect cannabinoids and/or reclaim the ethanol.

The temperature in the fixed bed reactor 212 is then raised to 800° C. During this third heating ramp, the cold trap 224 is disengaged from the exhaust line 232. $CO_2$ and/or water vapor are injected to the fixed bed reactor 212 using a boiler or steam generator 244 connected via a pipe 248 to the reactor.

The injected $CO_2$ and/or water vapor are run through a distributor plate or sparger distributor 252 set at the bottom of the fixed bed reactor 212. The distributor plate 252 distributes and diffuses $CO_2$ and/or water vapor to the milled spent cannabis biomass 204. The holes in the distributor plate 252 produce a homogeneous distribution of the introduced gas(ses), which pass upwards through the milled spent cannabis biomass 204. In some embodiments, the porosity of the distributor plate 252 is chosen to optimize the treatment of the milled spent cannabis biomass 204.

The temperature is maintained at 800° C. for 1 hour. After the process, activated carbon may be removed manually or automatically from the fixed bed reactor 212, or after the temperature has been reduced to about room temperature. The resulting activated carbon is then allowed to fully cool and stored at room temperature. Optionally, the activated carbon is stored in a sealed container. This prevents the activated carbon from absorbing latent compounds present in the environment.

In some embodiments, a larger condenser is used to capture cannabinoids evaporated from milled spent cannabis biomass with a higher expected return.

The treatment described herein is generally a low-cost process compared to other methods of producing activated carbon.

Figure 5:
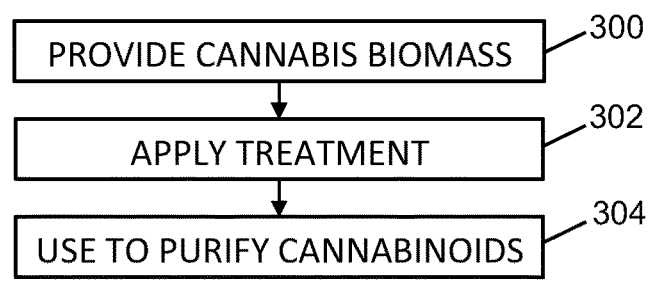
FIG. 5 is a high-level flowchart describing the process for using recycled, spent cannabis biomass in the purification of cannabinoids, according to an embodiment of the present invention.

Referring to FIG. 5, the spent cannabis biomass is provided in step 300. The spent cannabis biomass is treated in step 302 to form activated carbon. Then, in step 304, the activated carbon obtained during the treatment (step 302) is used in a purification process to filter out unwanted components in a cannabis extraction process. In this way, the cannabis from which cannabinoids are extracted is reused in a process to purify cannabinoids in a subsequent extraction process. This reduces the amount of waste generated by the cannabis industry.

E. Variations

This technique may also be used for denatured biomass. In this embodiment, denatured biomass is usually mixed with excess water and cat litter in order to be neutralized. In this case, the water capture step takes longer, but the end result, i.e. activated carbon, is the same.

In some embodiments, the spent cannabis biomass is dried in a dry room with a dehumidifier air controller, or it may be flash dried in a vacuum oven before or after the milling step 32.

This technique may also be used for fresh or dried cannabis (i.e. not spent), with a higher expected return of cannabinoid-rich oil. In this case a larger condenser volume would be advised.

In some embodiments, the fixed bed reactor 212 has a horizontal configuration instead of vertical, for treating larger batches of spent cannabis biomass.

In general, unless otherwise indicated, singular elements may be in the plural and vice versa with no loss of generality.

In some embodiments, the temperature for step 104 is maintained at a specified value with a ±10% range. In some embodiments, the temperature for step 112 is maintained at a specified value with a ±10% range.

Specified temperature values may be different in other embodiments. For example, the first temperature plateau may be set at anything from 80° C. to 120° C. The temperature of the second plateau may be set at anything between 170° C. to 230° C. In other embodiments, the second plateau may be set at a temperature between 170° C. and 500° C.

Time intervals may be different to the examples given herein. For example, the dwell times at the temperature plateaus may be different depending on the amount of biomass and the heating power of the flat bed reactor. The times taken for ramping the temperature may also be different.

In some embodiments, one or more intervening heating plateaus may be applied during the second heating ramp 108 in order to selectively evaporate one or more cannabinoids. The temperature for each intervening heating plateau is maintained at a given value with, say, a ±0.5° C. range. For example, the temperature may be maintained at a temperature of 230±0.5° C. ° C.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

Each embodiment provided herein provides one or more of the advantages described in relation to the invention, depending on its particular configuration.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the process. All parameters, dimensions and configurations described with respect to a specific embodiment are examples only and may be changed depending on the specific embodiment. Accordingly, the scope of the invention is to be construed in accordance with the substance defined by the following claims.

The invention claimed is:

1. A process for treating spent cannabis biomass comprising, in an oxygen-free atmosphere:
    raising the spent cannabis biomass to a first temperature that is sufficient to remove water and volatile components from the spent cannabis biomass;
    raising the spent cannabis biomass to a second temperature that is sufficient to reclaim cannabinoids from the spent cannabis biomass, wherein the second temperature is higher than the first temperature;
    raising to a third temperature the spent cannabis biomass, wherein the third temperature is higher than the second temperature; and
    injecting $CO_2$ and/or water vapor into the spent cannabis biomass at a flow rate of 100-3000 mL/min while the spent cannabis biomass is above the second temperature;
    thereby transforming the spent cannabis biomass into activated carbon.

2. The process of claim 1, comprising maintaining the spent cannabis biomass at the third temperature for 0.5 to 2 hours, wherein the third temperature is between 800 and 1000° C.

3. The process of claim 1, wherein the first temperature is 100±20° C. and the second temperature is 170-500° C.

4. The process of claim 1, wherein the first temperature is 100° C.

5. The process of claim 1, wherein the second temperature is 500° C.

6. The process of claim 1, wherein the spent cannabis biomass is heated in a fixed bed reactor.

7. The process of claim 6, wherein the fixed bed reactor has an exhaust line with a bypassable cold trap, the process comprising purging the fixed bed reactor with nitrogen before heating the spent cannabis biomass.

8. The process of claim 7, comprising, while raising the spent cannabis biomass to the first temperature, directing vapor evaporated from the spent cannabis biomass to bypass the cold trap.

9. The process of claim 7, comprising, while raising the spent cannabis biomass from the first temperature to the second temperature, passing vapor evaporated from the spent cannabis biomass through the cold trap.

10. The process of claim 1, wherein the $CO_2$ and/or water vapor is injected into the spent cannabis biomass using a boiler and a distributor plate.

11. The process of claim 1, comprising collecting the reclaimed cannabinoids by directing them into chilled ethanol.

12. The process of claim 1, comprising collecting the reclaimed cannabinoids with a condenser.

13. The process of claim 1, comprising maintaining the spent cannabis biomass at the first temperature until all the water is removed from the spent cannabis biomass.

14. The process of claim 1, comprising collecting water and volatile components from the spent cannabis biomass using a cold trap, while the spent cannabis biomass is below and at the first temperature.

15. The process of claim 1, comprising maintaining the spent cannabis biomass at the second temperature until all the cannabinoids have been reclaimed from the spent cannabis biomass.

16. The process of claim 1, comprising maintaining the spent cannabis biomass at the third temperature for 1 hour.

17. The process of claim 1, comprising milling the spent cannabis biomass to an average particle size below 2 mm prior to raising the spent cannabis biomass to the first temperature.

18. The process of claim 1, comprising passing nitrogen gas over the spent cannabis biomass throughout the process at a flow rate of 100-3000 mL/min.

* * * * *